United States Patent
Petersen (10) Patent No.: US 12,096,970 B2
(45) Date of Patent: Sep. 24, 2024

(54) MEDICAL SYSTEMS THAT IMPLEMENT A COMMON-MODE CHOKE TO REDUCE VOLTAGE TRANSIENTS

(71) Applicant: Intuitive Surgical Operations, Inc., Sunnyvale, CA (US)

(72) Inventor: Alan W. Petersen, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 811 days.

(21) Appl. No.: 17/282,460

(22) PCT Filed: Oct. 28, 2019

(86) PCT No.: PCT/US2019/058374
§ 371 (c)(1),
(2) Date: Apr. 2, 2021

(87) PCT Pub. No.: WO2020/092256
PCT Pub. Date: May 7, 2020

(65) Prior Publication Data
US 2021/0353352 A1 Nov. 18, 2021

Related U.S. Application Data (60) Provisional application No. 62/752,464, filed on Oct. 30, 2018.

(51) Int. Cl.
*A61B 18/12* (2006.01)
*A61B 34/00* (2016.01)
(Continued)

(52) U.S. Cl.
CPC .......... *A61B 18/1233* (2013.01); *A61B 34/70* (2016.02); *A61B 90/06* (2016.02);
(Continued)

(58) Field of Classification Search
CPC ..... A61B 18/1233; A61B 34/70; A61B 90/06; A61B 2090/064; A61B 2018/00178;
(Continued)

(56) References Cited

U.S. PATENT DOCUMENTS

2018/0132850 A1* 5/2018 Leimbach ........ A61B 17/07207

FOREIGN PATENT DOCUMENTS

WO WO-2015142822 A1 9/2015
WO WO-2017136357 A1 * 8/2017 ......... A61B 1/00018

OTHER PUBLICATIONS

International Preliminary Report on Patentability for Application No. PCT/US2019/058374, mailed on May 14, 2021, 11 pages.
(Continued)

*Primary Examiner* — Sameh R Boles (57) ABSTRACT

A medical system includes a first electrical circuit, a second electrical circuit electrically isolated from the first electrical circuit, an optical isolator circuit coupled between the first and second electrical circuits, and a common-mode choke comprising a plurality of wires wound around a core and configured to reduce a voltage transient at an input of the optical isolator circuit to a level within a tolerance of the optical isolator circuit. A first end of the wires is conductively coupled to an output of the first electrical circuit and a second end of the wires is conductively coupled to the input of the optical isolator circuit.

13 Claims, 6 Drawing Sheets

(51) Int. Cl.
    *A61B 90/00*         (2016.01)
    *H01F 17/06*         (2006.01)
    *A61B 18/00*         (2006.01)
    *A61B 18/14*         (2006.01)
    *H01F 17/00*         (2006.01)

(52) U.S. Cl.
    CPC .. *H01F 17/062* (2013.01); *A61B 2018/00178* (2013.01); *A61B 2018/00767* (2013.01); *A61B 2018/144* (2013.01); *A61B 2090/064* (2016.02); *H01F 2017/0093* (2013.01)

(58) Field of Classification Search
    CPC .... A61B 2018/00767; A61B 2018/144; H01F 17/062; H01F 2017/0093
    See application file for complete search history.

(56) References Cited

OTHER PUBLICATIONS

International Search Report and Written Opinion for Application No. PCT/US2019/058374, mailed Mar. 30, 2020, 15 pages.
Invitation to Pay Additional Fees and Partial International Search for PCT/US2019/058374, mailed Feb. 4, 2020, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

MEDICAL SYSTEMS THAT IMPLEMENT A COMMON-MODE CHOKE TO REDUCE VOLTAGE TRANSIENTS

RELATED APPLICATIONS

The present application is a U.S. National Stage Application under 35 U.S.C. § 371 of International Application No. PCT/US2019/058374, filed on Oct. 28, 2019, and entitled "MEDICAL SYSTEMS THAT IMPLEMENT A COMMON-MODE CHOKE TO REDUCE VOLTAGE TRANSIENTS", which claims priority to U.S. Provisional Patent Application No. 62/752,464, filed on Oct. 30, 2018, and entitled "MEDICAL SYSTEMS THAT IMPLEMENT A COMMON-MODE CHOKE TO REDUCE VOLTAGE TRANSIENTS," the contents of which are hereby incorporated by reference in their entirety.

BACKGROUND INFORMATION

During an electrosurgical procedure, such as during a minimally invasive surgical procedure that uses a computer-assisted surgical system, multiple surgical instruments may be concurrently located within a patient. For example, a surgeon may use an electrosurgical instrument to apply high voltage, high frequency electrical current to cauterize patient tissue. At the same time, the surgeon may use a force-sensing surgical instrument (e.g., force-sensing forceps, etc.) to position, move, hold in place, or otherwise manipulate the patient tissue and/or organs within the patient. The force-sensing surgical instrument may include one or more sensors configured to sense forces applied by the force-sensing surgical instrument. Data representative of the sensed forces may be transmitted by a first electrical circuit included in the force-sensing surgical instrument to a second electrical circuit included in a separate component to which the force-sensing surgical instrument is attached (e.g., a manipulator arm included in a computer-assisted surgical system). The second electrical circuit may process the data and/or relay the data to an external computing device, which may use the processed and/or relayed data to provide force-related information to the surgeon as the surgeon performs the electrosurgical procedure.

On some occasions, the electrosurgical instrument may inadvertently come in contact with the force-sensing surgical instrument while the electrosurgical instrument is being used to apply the high-voltage, high-frequency electrical current. If this happens, the electrical current may arc onto the force-sensing surgical instrument.

To prevent the electrical current from traveling to ground by way of the force-sensing surgical instrument and the component to which the force-sensing surgical instrument is attached, which could cause damage to various electronics and/or injury to the patient, an electrical isolation barrier may be implemented that electrically isolates the force-sensing surgical instrument from the component to which the force-sensing surgical instrument is attached. In this manner, an electrically conductive path between the first electrical circuit included in the instrument and the second electrical circuit included in the component is blocked.

To facilitate transmission of data (e.g.; force-sensing data) from the first electrical circuit across the isolation barrier to the second electrical circuit, an optical isolator circuit may be provided on the second electrical circuit. The optical isolator circuit is configured to optically transmit signals between the first and second electrical circuits, thus maintaining the electrical isolation between the two circuits.

But, a conventional optical isolator circuit cannot handle voltage transients (i.e., sudden changes in voltage) at its input that are outside a certain tolerance range. For example, a conventional optical isolator circuit may be configured to only be able to handle voltage transients at its input that are up to 100 Volts per nanosecond (V/ns). If a voltage transient greater than this amount (e.g., 400V/ns) is applied to the input of the optical isolator circuit, the optical isolator circuit may malfunction and/or the data path implemented by the optical isolator circuit may be corrupted.

SUMMARY

An exemplary medical system includes a first electrical circuit, a second electrical circuit electrically isolated from the first electrical circuit, an optical isolator circuit coupled between the first and second electrical circuits, wherein the optical isolator circuit is configured to optically transmit signals between the first and second electrical circuits, and a common-mode choke comprising a plurality of wires wound around a core and configured to reduce a voltage transient at an input of the optical isolator circuit to a level within a tolerance of the optical isolator circuit, wherein a first end of the wires is conductively coupled to an output of the first electrical circuit and a second end of the wires is conductively coupled to the input of the optical isolator circuit.

An exemplary surgical instrument includes a shaft configured to be inserted into a surgical area inside a patient, a tool at a distal end of the shaft, a sensor on at least one of the shaft and the tool and configured to output a signal, and a backend housing coupled to the shaft and configured to removably attach to a component separate from the surgical instrument. The backend housing includes a first electrical circuit and a common-mode choke. The first electrical circuit is configured to receive the signal from the sensor and transmit data representative of the signal to a second electrical circuit included in the component. The common-mode choke comprises a plurality of wires wound around a core. When the backend housing is removably attached to the component, a first end of the wires is conductively coupled to an output of the first electrical circuit, and a second end of the wires is conductively coupled to an input of an optical isolator circuit included in the component. The optical isolator circuit is configured to optically transmit signals between the first and second electrical circuits.

An exemplary computer-assisted surgical system includes a surgical instrument that comprises a first electrical circuit, a plurality of conductive feedthrough pins, and a common-mode choke comprising a plurality of wires wound around a core, a first end of the wires conductively coupled to an output of the first electrical circuit and a second end of the wires conductively coupled to the feedthrough pins. The computer-assisted surgical system further includes a manipulator arm configured to be selectively attached to the surgical instrument and that comprises a plurality of conductive receptacles configured to receive the feedthrough pins when the surgical instrument is attached to the manipulator arm, a second electrical circuit configured to be electrically isolated from the first electrical circuit when the manipulator arm is attached to the surgical instrument, and an optical isolator circuit coupled to an input of the second electrical circuit and to the plurality of receptacles and configured to optically transmit signals between the first and second electrical circuits when the manipulator arm is attached to the surgical instrument. The first electrical circuit is configured to transmit data to the second electrical circuit by way of the common-mode choke and the optical isolator circuit when the manipulator arm is attached to the surgical instrument.

An exemplary surgical instrument includes a shaft comprising a distal end, a tool at the distal end of the shaft, a sensor on at least one of the shaft and the tool, a common-mode electrical choke, an electrical connector, and a first electrical circuit coupled to receive a signal from the sensor and to output data representative of the signal via the common-mode choke to the electrical connector.

An exemplary surgical system includes a manipulator and a surgical instrument removably coupled to the manipulator. The surgical instrument comprises a shaft comprising a distal end, a tool at the distal end of the shaft, a sensor on at least one of the shaft and the tool, a common-mode electrical choke, a first electrical connector, and a first electrical circuit coupled to receive a signal from the sensor and to output data representative of the signal via the common-mode choke to the electrical connector. The manipulator comprises a second electrical connector removably coupled with the first electrical connector to receive the data representative of the signal, a second electrical circuit, and an optical isolator coupled to receive the data representative of the signal from the second electrical connector and to output optically isolated data representative of the data to the second electrical circuit.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Medical systems that implement a common-mode choke (also referred to as a common-mode electrical choke) to reduce voltage transients applied at an input of an optical isolator circuit are described herein. In some examples, a medical system includes a first electrical circuit (e.g., on a first printed circuit board ("PCB")), a second electrical circuit (e.g., on a second PCB) electrically isolated from the first electrical circuit, and an optical isolator circuit coupled between the first and second electrical circuits, wherein the optical isolator circuit is configured to optically transmit signals between the first and second electrical circuits. The medical system may further include a common-mode choke that includes a plurality of wires wound around a core. A first end of the wires is conductively coupled to an output of the first electrical circuit and a second end of the wires is conductively coupled to the input of the optical isolator circuit.

As will be described below, the common-mode choke may be configured to reduce a voltage transient (e.g., a voltage transient generated by an external source, such as an electrosurgical instrument) at an input of the optical isolator circuit to a level within a tolerance of the optical isolator circuit. This may advantageously allow the optical isolator circuit to function properly by transmitting signals (e.g., signals representative of data, power, and/or ground) between the first and second circuits without being negatively affected by the voltage transient.

To illustrate, the first electrical circuit may be housed within a backend of a surgical instrument, and the second electrical circuit may be housed within a manipulator arm carriage to which the backend of the surgical instrument is configured to attach. While attached to the manipulator arm carriage, the surgical instrument may be inserted into a surgical area of a patient and remotely controlled by a surgeon to perform one or more surgical procedures. While the surgical instrument is being used, the surgical instrument may generate data that is to be transmitted from the surgical instrument to an external computing device for processing and/or storage. For example, the surgical instrument may include one or more sensors configured to sense various parameters, such as force applied by the surgical instrument on patient tissue, temperature, movement of one or more objects, etc. Data representative of the sensed parameters may be transmitted by the first electrical circuit included in the surgical instrument to the second electrical circuit included in the manipulator arm carriage by way of the common-mode choke and the optical isolator circuit. The second electrical circuit may then transmit the received data to the external computing device.

In this configuration, the surgical instrument may inadvertently come in contact with an electrosurgical instrument that is also within the patient. For example, an active electrode at a distal end of the electrosurgical instrument, through which high voltage, high frequency electrical current is applied to patient tissue, may touch a metal portion (e.g., a metal tip or shaft) of the surgical instrument. When this touch happens, the electrical current may arc onto the surgical instrument and create a voltage transient at the input of the optical isolator circuit. This voltage transient may be relatively large (e.g., around 400 V/ns). But, the optical isolator circuit may only be able to tolerate voltage transients up to 100V/ns. By having an appropriately configured common-mode choke inserted into the data transmission path between the first electrical circuit and the input to the optical isolator circuit, however, the voltage transient may be reduced to a level that is within a tolerance of the optical isolator circuit.

Figure 1:
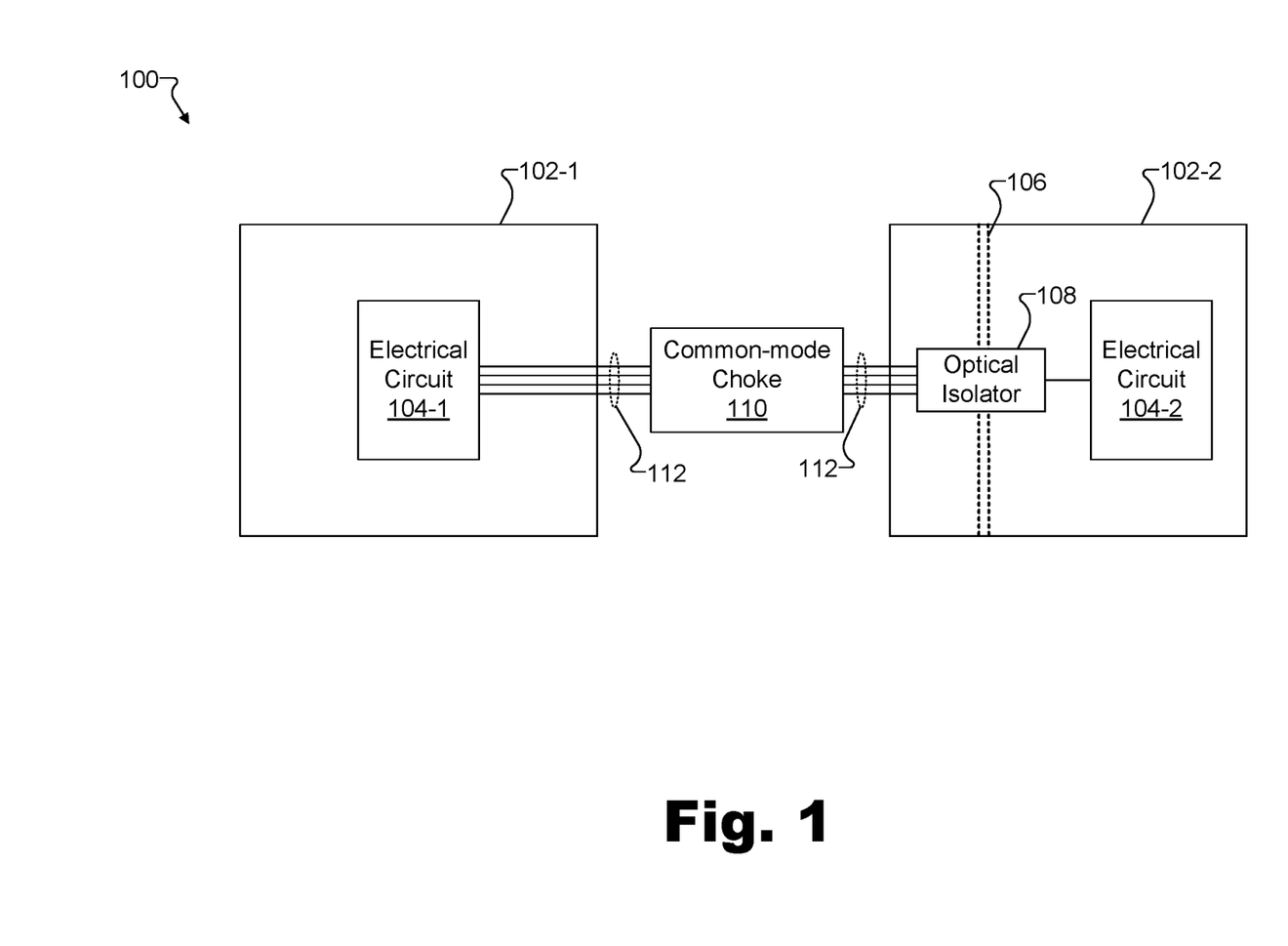
FIG. 1 shows an exemplary medical system according to principles described herein.

FIG. 1 shows an exemplary medical system 100. As shown, medical system 100 includes a first PCB 102-1 and a second PCB 102-2. A first electrical circuit 104-1 is on PCB 102-1, and second electrical circuit 104-2 is on second PCB 102-2. While electrical circuits 104 are shown as being on PCBs, one or both of electrical circuits 104 may alternatively not be on PCBs.

PCBs 102 are configured to mechanically support and electrically couple various electrical components included in electrical circuits 104. For example, PCBs 102 may each include conductive pads, to which electrical components may be soldered or otherwise electrically coupled, and conductive paths (e.g., traces, vias, etc.) that electrically interconnect the various electrical components. In some examples, non-conductive components (e.g., a housing of an optical isolator circuit) may be attached (e.g., mechanically fastened, etc.) to either of PCBs 102.

Electrical circuits 104 may each include any suitable combination of electrical components configured to perform various functions. For example, electrical circuit 104-1 may be configured to generate data for transmission to electrical circuit 104-2. Likewise, electrical circuit 104-2 may be configured to receive the data transmitted by electrical circuit 104-1. Electrical circuit 104-2 may be further configured to transmit power and ground signals to electrical circuit 104-1.

As shown, an electrical isolation barrier 106 is on PCB 102-2. Electrical isolation barrier 106 electrically isolates electrical circuit 104-2 from electrical circuit 104-1. In other words, electrical isolation barrier 106 prevents any component included in electrical circuit 104-2 from being electrically connected in any way to any component included in electrical circuit 104-1. Electrical isolation barrier 106 may be implemented in any suitable manner, such as an optical isolator circuit.

To facilitate transmission of signals between electrical circuits 104-1 and 104-2 across electrical isolation barrier 106, medical system 100 includes an optical isolator circuit 108. Optical isolator circuit 108 is configured to optically transmit signals between electrical circuits 104.

As shown, medical system 100 further includes a common-mode choke 110 in a signal transmission path between electrical circuit 104-1 and electrical circuit 104-2. As will be described in more detail below, common-mode choke 110 includes a plurality of wires 112 wound around a core (not shown). A first end of wires 112 is conductively coupled to an output of electrical circuit 104-1. A second end of wires 112 may be communicatively coupled to an input of optical isolator circuit 108 (e.g., when a component that houses PCB 102-1 is attached to a component that houses PCB 102-2, as will be described in more detail below).

Figure 2A:
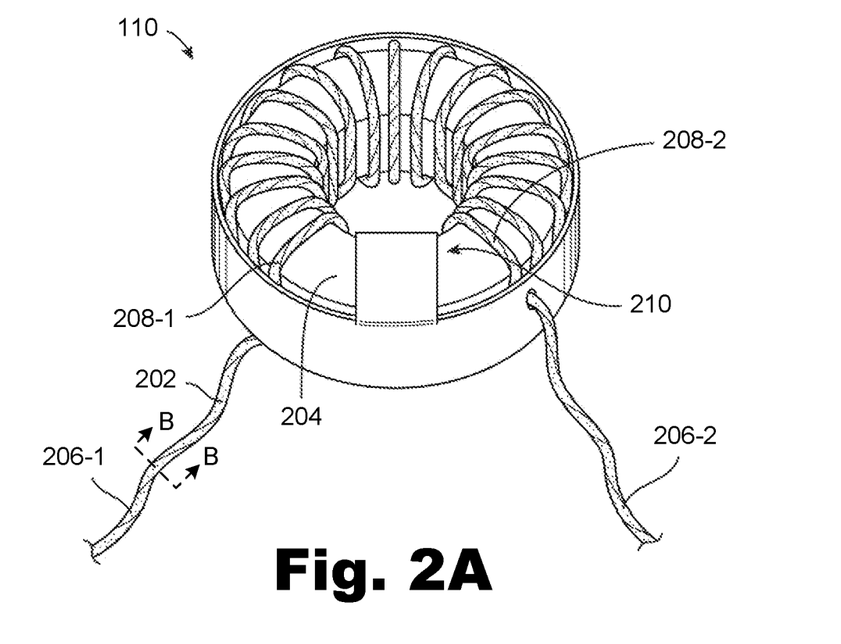
FIG. 2A is an illustration of common-mode choke according to principles described herein.

FIG. 2A is an illustration of common-mode choke 110. As shown, common-mode choke 110 includes a cable 202 that is wound around a closed (e.g., toroidal) core 204. An input side 206-1 of cable 202 is configured to be routed and conductively coupled to electrical circuit 104-1, and an output side 206-2 of cable 202 is configured to be routed and conductively coupled to electrical circuit 104-2.

Figure 2B:
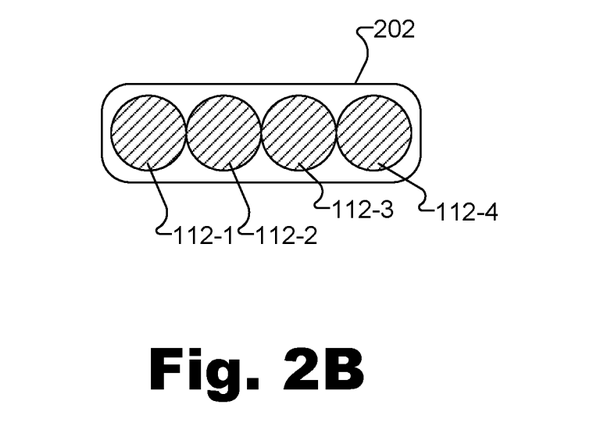
FIG. 2B shows a cross-sectional view of a cable of the common-mode choke of FIG. 2A according to principles described herein.

FIG. 2B shows a cross-sectional view of cable 202 taken along the perspective lines B-B in FIG. 2A. As shown, cable 202 houses four wires 112. A first wire 112-1 is configured to carry a power signal from electrical circuit 104-2 to electrical circuit 104-1. A second wire 112-2 is configured to carry a ground signal from electrical circuit 104-2 to electrical circuit 104-1. A third wire 112-3 is configured to carry data from electrical circuit 104-1 to electrical circuit 104-2. A fourth wire 112-4 is configured to carry data from electrical circuit 104-2 to electrical circuit 104-1. While four wires 112 are shown in FIG. 2B, it will be recognized that any number of wires may be included in cable 202 as may serve a particular implementation.

Each of wires 112 are individually insulated. Hence, in some examples, cable 202 may be omitted and wires 112 may be individually wound around core 204 as a set.

As shown in FIG. 2B, wires 112 are parallel, one with another, within cable 202. For example, wires 112 may be parallel bonded to ensure they stay parallel one with another while cable 202 is wound around core 204. This multifilar arrangement advantageously ensures that interference (e.g., interference caused by arcing voltage from an electrosurgical instrument) introduced onto one of wires 112 is equally shared on all of wires 112. This arrangement helps maximize a reduction in voltage transients achieved by common-mode choke 110. In some alternative configurations, wires 112 may be twisted about one another.

As shown in FIG. 2A, cable 202 (i.e., wires 112) are wound around core 204 in a sequence of windings 208 starting with an input winding 208-1 and ending with an output winding 208-2.

As shown, windings are non-overlapping (i.e., none of windings 208 overlap one with another). Avoiding overlap of windings 208 has several advantages. For example, non-overlapping minimizes the capacitance created between each adjacent windings 208, and this minimization of capacitance helps to minimize the input-to-output capacitance of common-mode choke 110. Moreover, non-overlapping windings 208 prevent arcing that would occur between overlapping windings in the event of individual wire insulation failure.

As shown, input winding 208-1 is separated on core 204 from output winding 208-2 by a gap 210. Gap 210 is at least a predetermined threshold distance along a perimeter of core 204 (e.g., at least around fifteen percent of the perimeter of core 204). Gap 210 may minimize capacitive coupling between input winding 208-1 and output winding 208-2, which increases the effectiveness of common-mode choke 110 in reducing voltage transients.

Common-mode choke 110 may include any suitable number of windings 208. An increase in the number of windings 208 may increase voltage transient reduction achievable by common-mode choke 110. Hence, in some examples, the number of windings 208 may be maximized while still ensuring that each winding 208 does not overlap with any other winding 208 and that gap 210 between input winding 208-1 and output winding 208-2 is maintained.

Core 204 may be made out of any suitable material. In some examples, the material of core 204 is selected to achieve maximum impedance and voltage transient reduction at arcing electrosurgical frequencies (e.g., around 10 MHz). In some examples, core 204 is a ferrite torpid core or a ferrite bobbin/pot core. Alternatively, core 204 may be a nano-crystalline ferrite core without a gap. This nano-crystalline ferrite core material provides a relatively higher inductance per turn compared to other core materials, which results in less stray capacitance from input side 206-1 to output side 206-2 of cable 202. In another embodiment, core 204 is a nanocrystalline ferrite core in a plastic casing, Core 204 may have any suitable dimensions, inductance, and/or other characteristic as may serve a particular implementation.

Figure 3:
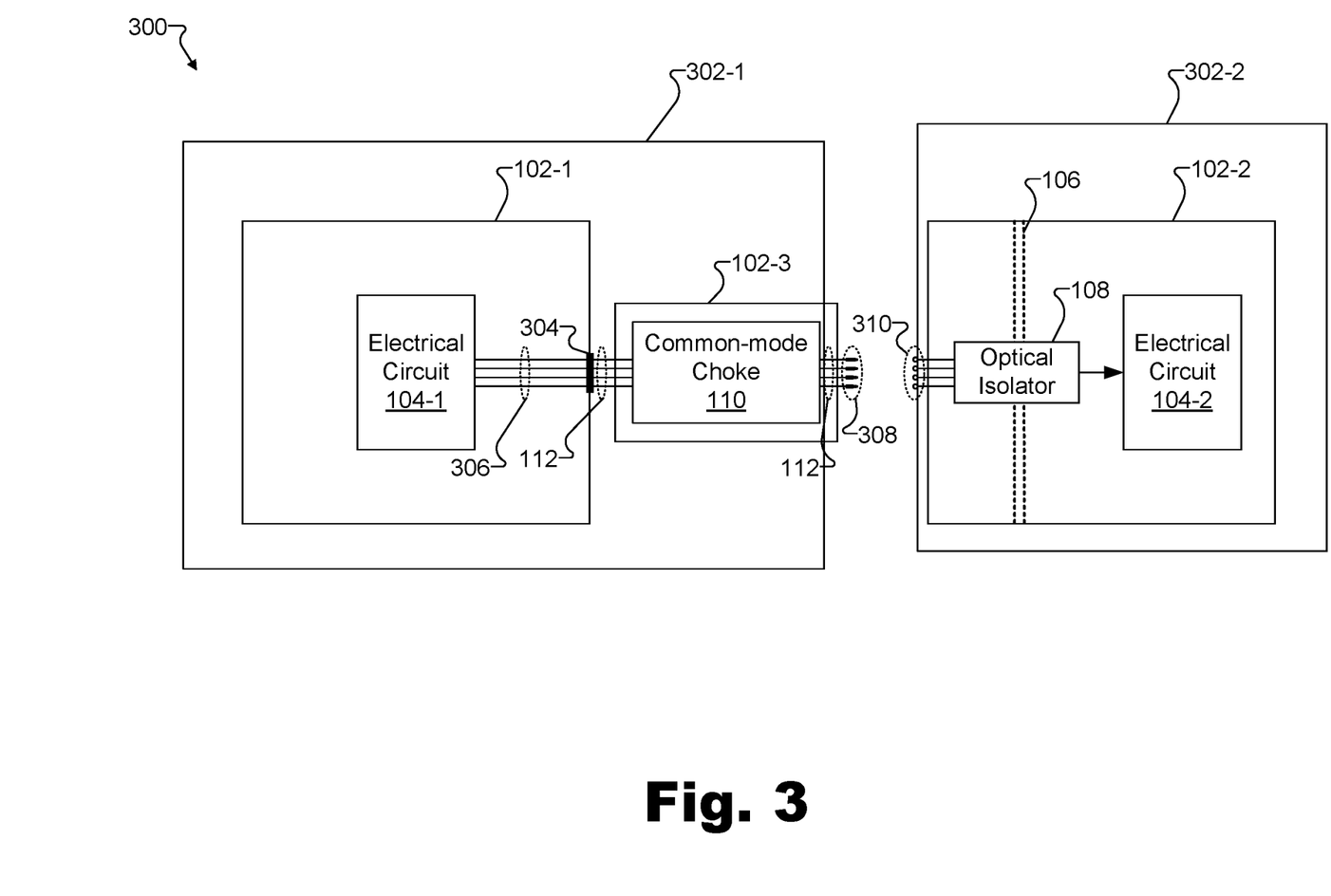
FIG. 3 shows an exemplary implementation of the medical system of FIG. 1 according to principles described herein.

FIG. 3 shows an exemplary implementation 300 of medical system 100 (FIG.

1). In implementation 300, PCB 102-1 and common-mode choke 110 are included in a first component 302-1, and PCB 102-2 is included in a second component 302-2. Component 302-1 is configured to selectively attach to component 302-2. Components 302 may each be implemented by separate housings such that component 302-1 is not in physical or communicative contact with component 302-2 when component 302-1 is not attached to component 302-2.

Components 302 may each be implemented by any suitable electronic device configured to be selectively attached to and communicate with another electronic device. For example, as will be illustrated below, component 302-1 may be implemented by a surgical instrument included in a computer-assisted surgical system, and component 302-2 may be implemented by a manipulator arm that is also included in the computer-assisted surgical system. While attached one to another, components 302 may be remotely controlled by a surgeon or other user in order to perform one or more operations included in a surgical procedure.

In the example of FIG. 3, common-mode choke 110 is on a PCB 102-3 included in component 302-1 and separate from PCB 102-1. In this configuration, the input side of wires 112 may be configured to selectively connect to (e.g., plug into) a receiving port 304 on PCB 102-1, Receiving port 304 may be conductively coupled to traces 306 on PCB 102-1 that provide a conductive path to electrical circuit 104. In this manner, the input side of wires 112 may be conductively coupled to electrical circuit 104-1.

As shown, wires 112 at an output side are conductively connected to feedthrough pins 308, which illustrate and function as an electrical connector. Feedthrough pins 308 extend away from component 302-1 and may be implemented in any suitable manner. For example, feedthrough pins 308 may be implemented by pogo pins or any other suitable type of feedthrough.

As shown, component 302-2 includes a plurality of conductive receptacles 310 conductively coupled to the input of optical isolator circuit 108. These receptacles 310 illustrate and function as an electrical connector and are configured to receive feedthrough pins 308 when component 302-1 is attached to component 302-2. In this manner, feedthrough pins 308 and receptacles 310 provide conductive coupling of wires 112 to the input of optical isolator circuit 108.

While common-mode choke 110 is shown to be on its own PCB 102-3 in FIG. 3, it will be recognized that common-mode choke 110 may alternatively be located elsewhere within medical system 100. For example, common-mode choke 110 may be on PCB 102-1 or on PCB 102-2, or on some other component within medical system 100.

As mentioned, components 302 may be included in a computer-assisted surgical system. For example, component 302-1 may be implemented by a surgical instrument having a distal portion configured to be inserted into a surgical area of a patient, and component 302-2 may be implemented by a manipulator arm to which the surgical instrument may attach in order to be remotely controlled by a surgeon using the computer-assisted surgical system. An exemplary computer-assisted surgical system within which components 302 may be implemented will now be described.

Figure 4:
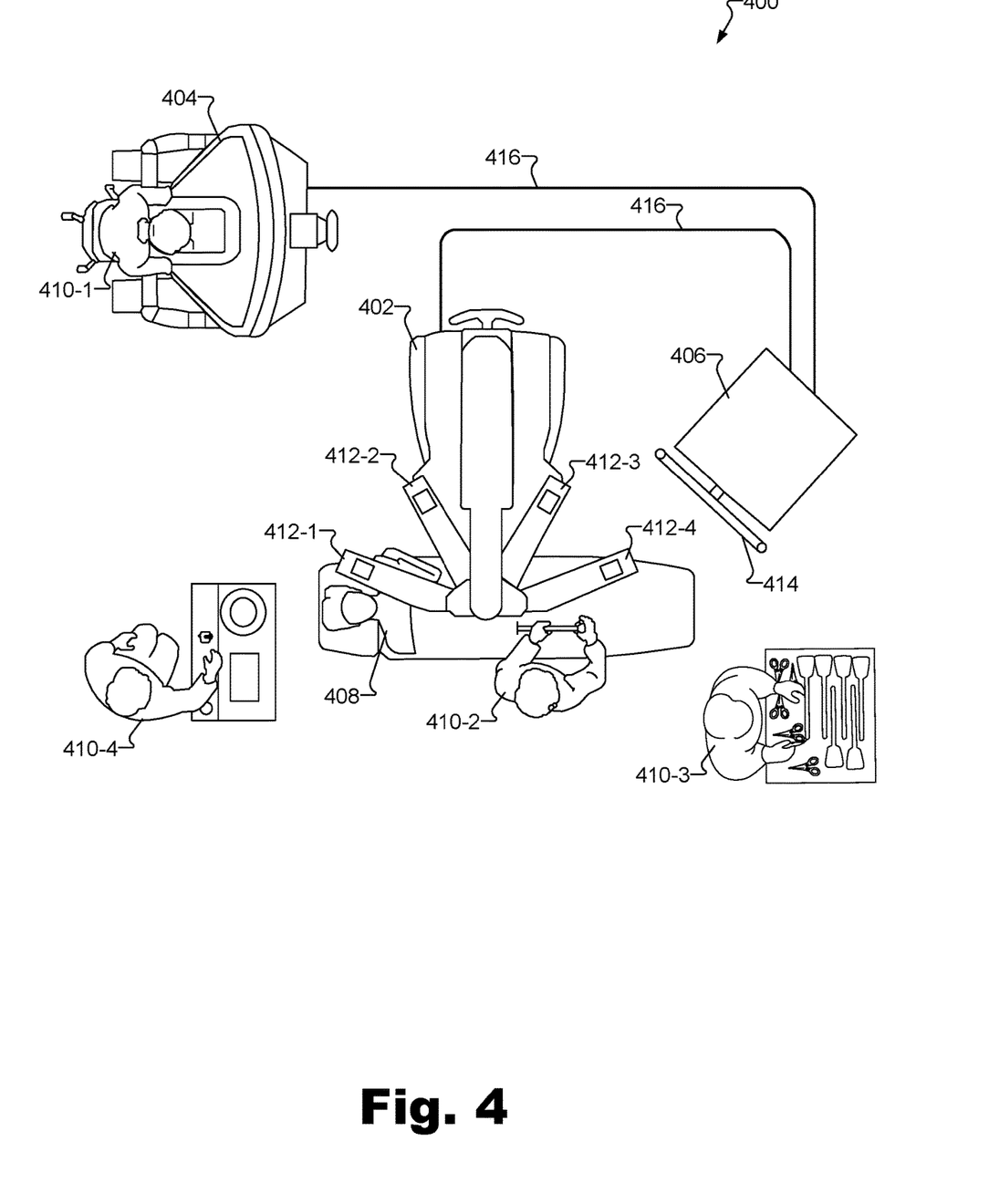
FIG. 4 illustrates an exemplary computer-assisted surgical system according to principles described herein.

FIG. 4 illustrates an exemplary computer-assisted surgical system 400 ("surgical system 400"). As shown, surgical system 400 may include a manipulating system 402, a user control system 404, and an auxiliary system 406 communicatively coupled one to another. Surgical system 400 may be used by a surgical team to perform a computer-assisted surgical procedure on a patient 408. As shown, the surgical team may include a surgeon 410-1, an assistant 410-2, a nurse 410-3, and an anesthesiologist 410-4, all of whom may be collectively referred to as "surgical team members 410." Additional or alternative surgical team members may be present during a surgical session as may serve a particular implementation.

While FIG. 4 illustrates an ongoing minimally invasive surgical procedure, it will be understood that surgical system 400 may similarly be used to perform open surgical procedures or other types of surgical procedures that may similarly benefit from the accuracy and convenience of surgical system 400. Additionally, it will be understood that the surgical session throughout which surgical system 400 may be employed may not only include an operative phase of a surgical procedure, as is illustrated in FIG. 4, but may also include preoperative, postoperative, and/or other suitable phases of the surgical procedure.

As shown in FIG. 4, manipulating system 402 may include a plurality of manipulator arms 412 (e.g., manipulator arms 412-1 through 412-4) to which a plurality of surgical instruments may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure on patient 408 (e.g., by being at least partially inserted into patient 408 and manipulated to perform a computer-assisted surgical procedure on patient 408). In some examples, one or more of the surgical instruments may include force-sensing and/or other sensing capabilities. While manipulating system 402 is depicted and described herein as including four manipulator arms 412, it will be recognized that manipulating system 402 may include only a single manipulator arm 412 or any other number of manipulator arms as may serve a particular implementation.

Manipulator arms 412 and/or surgical instruments attached to manipulator arms 412 may include one or more displacement transducers, orientational sensors, and/or positional sensors used to generate raw (i.e., uncorrected) kinematics information. One or more components of surgical system 400 may be configured to use the kinematics information to track (e.g.; determine positions of) and/or control the surgical instruments.

Surgical instruments attached to manipulator arms 412 may each be positioned at a surgical area associated with a patient. As used herein, a "surgical area" associated with a patient may, in certain examples, be entirely within the patient and may include an area within the patient near where a surgical procedure is planned to be performed, is being performed, or has been performed. For example, for a minimally invasive surgical procedure being performed on tissue internal to a patient, the surgical area may include the tissue as well as space around the tissue where, for example, surgical instruments being used to perform the surgical procedure are located. In other examples, a surgical area may be at least partially external to the patient. For instance, surgical system 400 may be used to perform an open surgical procedure such that part of the surgical area (e.g., tissue being operated on) is internal to the patient while another part of the surgical area (e.g., a space around the tissue where one or more surgical instruments may be located) is external to the patient. A surgical instrument may be referred to as being located at or within a surgical area when at least a portion of the surgical instrument (e.g., a distal end of the surgical instrument) is located within the surgical area.

User control system 404 may be configured to facilitate control by surgeon 410-1 of manipulator arms 412 and surgical instruments attached to manipulator arms 412. For example, surgeon 410-1 may interact with user control system 404 to remotely move or manipulate manipulator arms 412 and the surgical instruments. To this end, user control system 404 may provide surgeon 410-1 with imagery (e.g., high-definition 3D imagery) of a surgical area associated with patient 408 as captured by an endoscope. In certain examples, user control system 404 may include a stereo viewer having two displays where stereoscopic images of a surgical area associated with patient 408 and generated by a stereoscopic endoscope may be viewed by surgeon 410-1. Surgeon 410-1 may use the imagery to perform one or more procedures with one or more surgical instruments attached to manipulator arms 412.

To facilitate control of surgical instruments, user control system 404 may include a set of master controls. These master controls may be manipulated by surgeon 410-1 to control movement of surgical instruments (e.g., by utilizing robotic and/or teleoperation technology). The master controls may be configured to detect a wide variety of hand, wrist, and finger movements by surgeon 410-1. In this manner, surgeon 410-1 may intuitively perform a procedure using one or more surgical instruments.

Auxiliary system 406 may include one or more computing devices configured to perform primary processing operations of surgical system 400. In such configurations, the one or more computing devices included in auxiliary system 406 may control and/or coordinate operations performed by various other components (e.g., manipulating system 402 and user control system 404) of surgical system 400. For example, a computing device included in user control system 404 may transmit instructions to manipulating system 402 by way of the one or more computing devices included in auxiliary system 406. As another example, auxiliary system 406 may receive, from manipulating system 402, and process image data representative of imagery captured by an endoscope attached to one of manipulator arms 412.

In some examples, auxiliary system 406 may be configured to present visual content to surgical team members 410 who may not have access to the images provided to surgeon 410-1 at user control system 404. To this end, auxiliary system 406 may include a display monitor 414 configured to display one or more user interfaces, such as images (e.g., 2D images) of the surgical area, information associated with patient 408 and/or the surgical procedure, and/or any other visual content as may serve a particular implementation. For example, display monitor 414 may display images of the surgical area together with additional content (e.g., graphical content, contextual information, etc.) concurrently displayed with the images. In some embodiments, display monitor 414 is implemented by a touchscreen display with which surgical team members 410 may interact (e.g., by way of touch gestures) to provide user input to surgical system 400.

Manipulating system 402, user control system 404, and auxiliary system 406 may be communicatively coupled one to another in any suitable manner. For example, as shown in FIG. 4, manipulating system 402, user control system 404, and auxiliary system 406 may be communicatively coupled by way of control lines 416, which may represent any wired or wireless communication link as may serve a particular implementation. To this end, manipulating system 402, user control system 404, and auxiliary system 406 may each include one or more wired or wireless communication interfaces, such as one or more local area network interfaces, Wi-Fi network interfaces, cellular interfaces, etc.

Figure 5A:
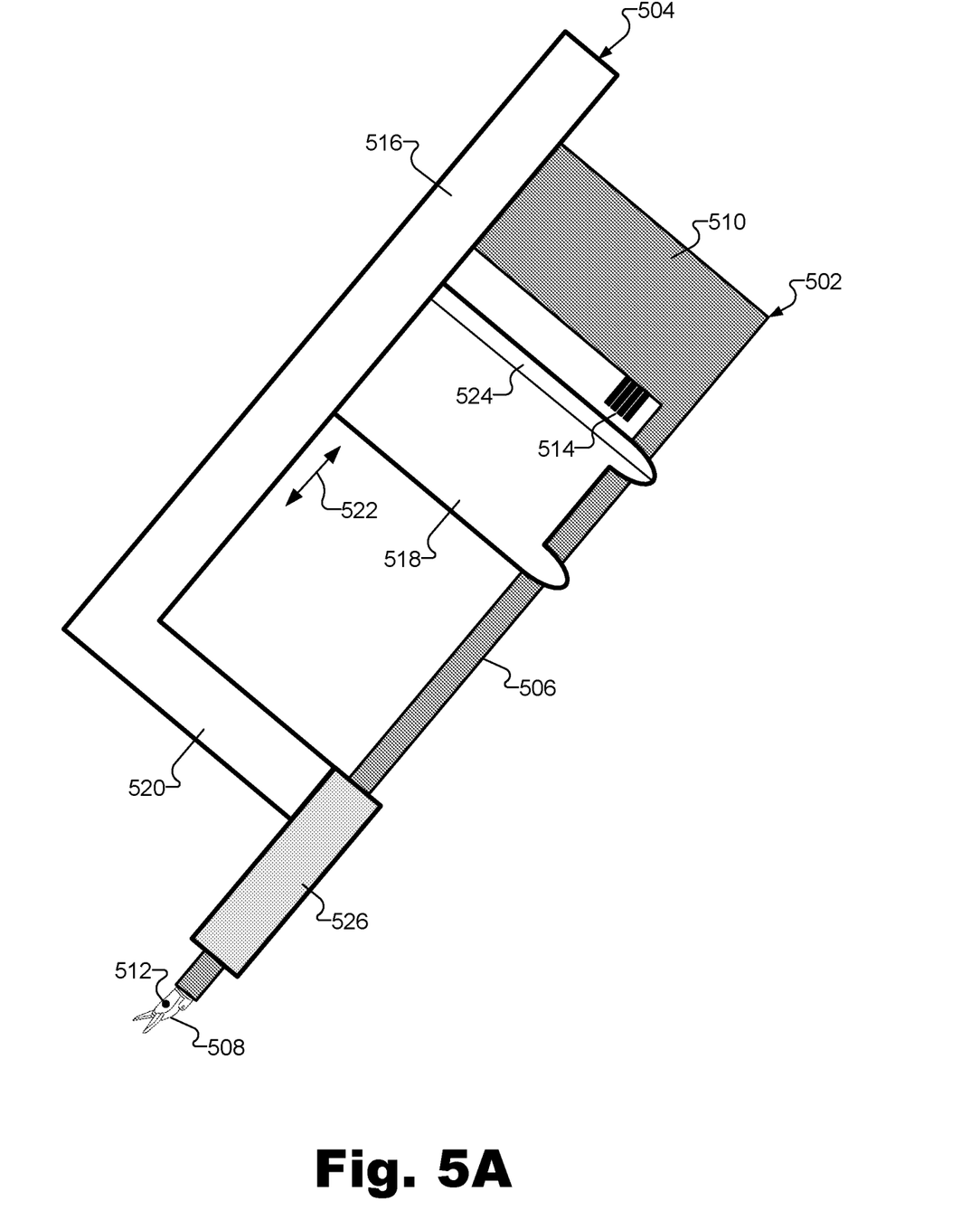
FIGS. 5A-5B show an attachment of a surgical instrument to a manipulator arm according to principles described herein.
Figure 5B:
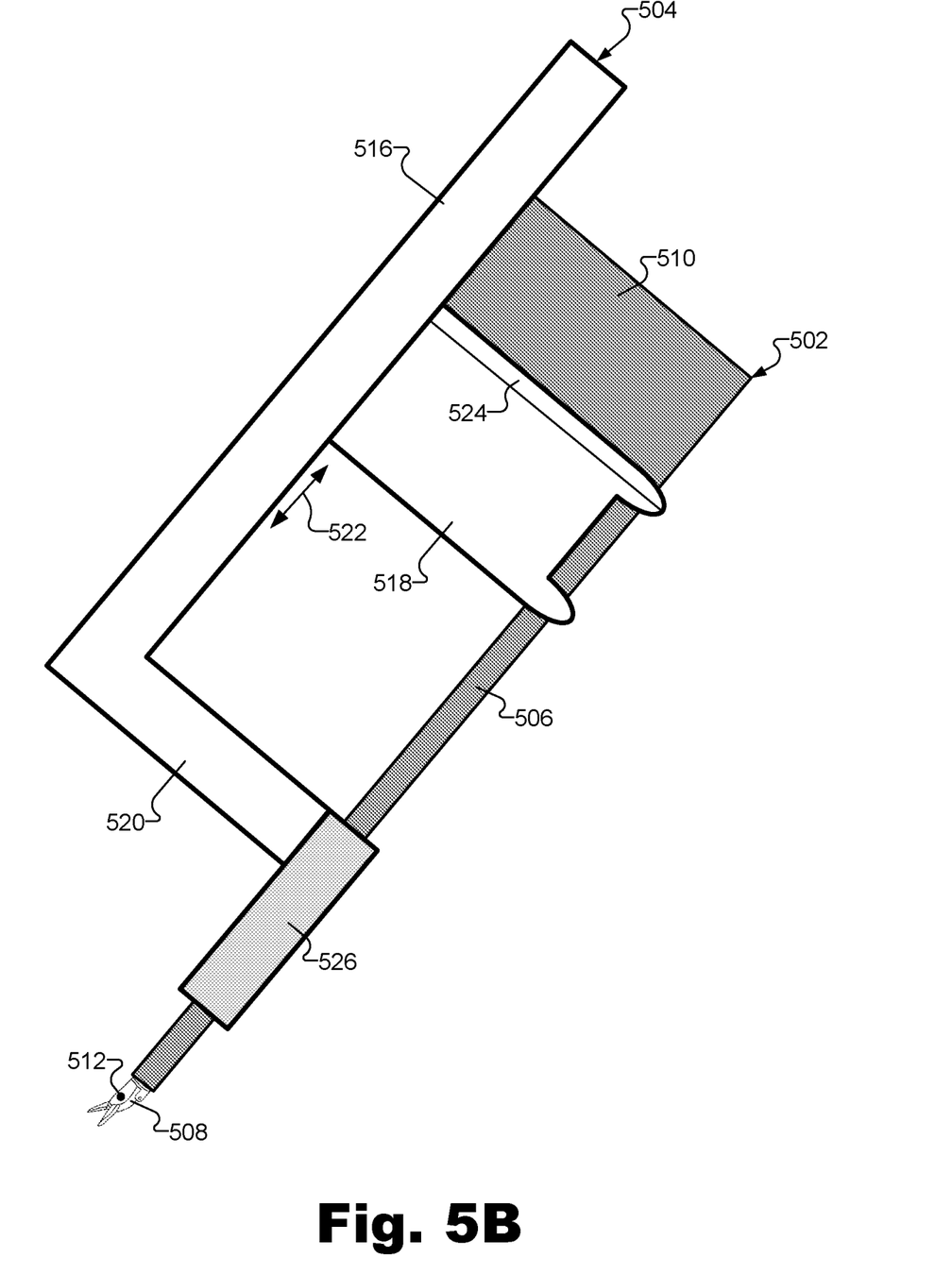

FIG. 5A shows a surgical instrument 502 just prior to being attached to a manipulator arm 504, and FIG. 5B shows surgical instrument 502 attached to manipulator arm 504. Manipulator arm 504 may implement one of manipulator arms 412 of surgical system 400.

As shown, surgical instrument 502 includes a shaft 506, a tool 508 at a distal end of shaft 506, and a backend housing 510 coupled to shaft 506. A sensor 512 is shown to be included on tool 508. Sensor 512 may additionally or alternatively be on shaft 506 or any other portion of surgical instrument 502.

In some examples, backend housing 510 implements component 302-1. Hence, in these examples, backend housing 510 houses PCB 102-1, electrical circuit 104-1, and common-mode choke 110. Feedthrough pins 520 are conductively coupled to an output of common-mode choke 110 and, as shown, extend away from backend housing 510.

As shown, manipulator arm 504 includes a main frame 516, a carriage 518 (also referred to herein as a manipulator arm carriage), and a cannula coupling member 520. Main frame 516 may include a track or channel (not shown) to which carriage 518 is attached and along which carriage 518 may slidably move in either direction, as depicted by arrow 522.

In some examples, carriage 518 implements component 302-2. Hence, in these examples, carriage 518 houses PCB 102-2, electrical circuit 104-2, and optical isolator circuit 108. As shown, carriage 518 may include a non-conductive sterile adapter element 524 configured to be in physical contact with backend housing 510 when surgical instrument 502 is attached to manipulator arm 504, Sterile adapter element 524 may be made out of any suitable non-conductive material (e.g., plastic).

To facilitate attachment of surgical instrument 502 (i.e., backend housing 510) to manipulator arm 504 (i.e., carriage 518), a plurality of receptacles (not shown) may be included in sterile adapter element 524 and positioned to align with feedthrough pins 514. The receptacles receive feedthrough pins 514 when backend housing 510 is attached to carriage 518, thus conductively coupling the output of common-mode choke 110 with the input of optical isolator circuit 108.

Cannula coupling member 520 extends away from main frame 516 and is configured to selectively attach to a cannula 526. Cannula 526 may be inserted through a port into a surgical area inside a patient. As shown, shaft 506 may pass through cannula 526 to enter the surgical area.

While surgical instrument 502 is attached to manipulator arm 504, sensor 512 may output a signal (e.g., a signal representative of an amount of force applied by tool 508 on patient tissue). Electrical circuit 104-1 is configured to receive the signal output by sensor 512 and transmit the signal (or data representative of the signal) to electrical circuit 104-2 by way of common-mode choke 110 and optical isolator circuit 108. Electrical circuit 104-2 may process the signal and/or transmit the signal to another component (e.g., auxiliary system 406).

While a distal portion of surgical instrument 502 (i.e., tool 508) is within a patient, tool 508 may inadvertently come in contact with an electrosurgical instrument that is also within the patient. For example, an active electrode at a distal end of the electrosurgical instrument, through which high voltage, high frequency electrical current is applied to patient tissue, may touch tool 508. The arc may create a large voltage transient in instrument 502. Common-mode choke 110 included in backend housing 510 reduces this voltage transient to a level that is within a tolerance of optical isolator circuit 108 within carriage 518 before the voltage transient reaches the input of optical isolator circuit 108.

In some examples, a surgical instrument (e.g., surgical instrument 502) may include a shaft comprising a distal end, a tool at the distal end of the shaft, a sensor on at least one of the shaft and the tool, a common-mode electrical choke, an electrical connector, and a first electrical circuit coupled to receive a signal from the sensor and to output data representative of the signal via the common-mode choke to the electrical connector, Each of these elements may be implemented by any of the components described herein. In some examples, the signal from the sensor represents of an amount of force applied by the tool. In some examples, the common-mode electrical choke is tuned to impede a high frequency, high voltage signal from an electrosurgical instrument.

In some examples, a surgical system includes a manipulator (e.g., a manipulator arm as described herein) and a surgical instrument (e.g., surgical instrument 502) removably coupled to the manipulator. The surgical instrument includes a shaft comprising a distal end, a tool at the distal end of the shaft, a sensor on at least one of the shaft and the tool, a common-mode electrical choke, a first electrical connector, and a first electrical circuit coupled to receive a signal from the sensor and to output data representative of the signal via the common-mode choke to the electrical connector. The manipulator includes a second electrical connector removably coupled with the first electrical connector to receive the data representative of the signal, a second electrical circuit, and an optical isolator coupled to receive the data representative of the signal from the second electrical connector and to output optically isolated data representative of the data to the second electrical circuit. In some examples, the signal from the sensor represents of an amount of force applied by the tool. In some examples, the common-mode electrical choke is tuned to impede a high frequency, high voltage signal from an electrosurgical instrument.

In the preceding description, various exemplary embodiments have been described with reference to the accompanying drawings. It will be evident that various modifications and changes may be made thereto, however, and additional embodiments may be implemented without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A surgical instrument, comprising:
    a shaft configured to be inserted into a surgical area inside a patient;
    a tool at a distal end of the shaft;
    a sensor on at least one of the shaft and the tool and configured to output a signal; and
    a backend housing coupled to the shaft and configured to removably attach to a component separate from the surgical instrument, the backend housing comprising a first electrical circuit and a common-mode choke, the component comprising a carriage attached to a main frame of a manipulator arm of a surgical system and configured to slidably move along the main frame;
    wherein the first electrical circuit is configured to receive the signal from the sensor and transmit data representative of the signal to a second electrical circuit included in the component;
    wherein the common-mode choke comprises a plurality of wires wound around a core;
    wherein, when the backend housing is removably attached to the component, the common-mode choke is coupled between the first electrical circuit and an optical isolator circuit included in the component; and
    wherein the optical isolator circuit is configured to optically transmit signals between the first and second electrical circuits.

2. The surgical instrument of claim 1, wherein:
    the sensor is configured to detect a force between the tool and an object; and
    the data is representative of the force.

3. The surgical instrument of claim 1, further comprising a plurality of conductive feedthrough pins conductively coupled to a plurality of wires of the common-mode choke, wherein the feedthrough pins are configured to be conductively coupled to an input of the optical isolator circuit when the backend housing is attached to the component.

4. The surgical instrument of claim 1, wherein the common-mode choke comprises a plurality of wires wound around a core, the plurality of wires comprising:
    a first wire configured to carry a power signal from the second electrical circuit to the first electrical circuit; and
    a second wire configured to connect a ground of the first electrical circuit with a ground of the second electrical circuit.

5. The surgical instrument of claim 4, wherein the plurality of wires further comprises:
    a third wire configured to carry data from the first electrical circuit to the second electrical circuit; and
    a fourth wire configured to carry data from the second electrical circuit to the first electrical circuit.

6. The surgical instrument of claim 5, wherein the data carried by the third wire from the first electrical circuit to the second electrical circuit comprises the data representative of the signal.

7. The surgical instrument of claim 1, wherein the common-mode choke comprises a plurality of wires wound around a core in a plurality of non-overlapping windings.

8. The surgical instrument of claim 7, wherein an input winding in the plurality of non-overlapping windings is separated on the core from an output winding in the plurality of non-overlapping windings by a gap.

9. A surgical system, comprising:
    a manipulator comprising a main frame and a carriage configured to slidably move along the main frame;
    a surgical instrument removably coupled to the carriage;
    wherein the surgical instrument comprises a shaft comprising a distal end, a tool at the distal end of the shaft, a sensor on at least one of the shaft and the tool, a common-mode electrical choke, a first electrical connector, and a first electrical circuit coupled to receive a signal from the sensor and to output data representative of the signal via the common-mode choke to the electrical connector; and
    wherein the manipulator comprises a second electrical connector removably coupled with the first electrical connector to receive the data representative of the signal, a second electrical circuit, and an optical isolator coupled to receive the data representative of the signal from the second electrical connector and to output optically isolated data representative of the data to the second electrical circuit.

10. The surgical system of claim 9, wherein the signal from the sensor represents of an amount of force applied by the tool.

11. The surgical system of claim 10, wherein the common-mode electrical choke is tuned to impede a high frequency, high voltage signal from an electrosurgical instrument.

12. The surgical system of claim 9, wherein the common-mode choke comprises a plurality of wires wound around a core.

13. The surgical system of claim 12, wherein the plurality of wires is wound around the core in a plurality of non-overlapping windings.

* * * * *